(12) United States Patent
Li et al.

(10) Patent No.: US 12,172,014 B2
(45) Date of Patent: Dec. 24, 2024

(54) SYSTEMS AND METHODS FOR DELIVERING NEUROMODULATION TO REDUCE CORTICAL SPREADING DEPOLARIZATION IN ANIMALS INCLUDING HUMANS

(71) Applicant: The Feinstein Institutes for Medical Research, Manhasset, NY (US)

(72) Inventors: Chunyan Li, Manhasset, NY (US); Raj Kumar Narayan, Manhasset, NY (US)

(73) Assignee: The Feinstein Institutes For Medical Research, Manhasset, NY (US)

( * ) Notice: Subject to any disclaimer, the term of this patent is extended or adjusted under 35 U.S.C. 154(b) by 426 days.

(21) Appl. No.: 17/606,364

(22) PCT Filed: Apr. 26, 2019

(86) PCT No.: PCT/US2019/029382
§ 371 (c)(1),
(2) Date: Oct. 25, 2021

(87) PCT Pub. No.: WO2020/219072
PCT Pub. Date: Oct. 29, 2020

(65) Prior Publication Data
US 2022/0233859 A1    Jul. 28, 2022

(51) Int. Cl.
*A61N 1/36* (2006.01)
*A61B 5/316* (2021.01)
*A61N 1/04* (2006.01)

(52) U.S. Cl.
CPC .......... *A61N 1/36025* (2013.01); *A61B 5/316* (2021.01); *A61N 1/0456* (2013.01); *A61N 1/36031* (2017.08); *A61N 1/36034* (2017.08)

(58) Field of Classification Search
CPC ............ A61N 1/36025; A61N 1/36082; A61N 1/36034; A61N 1/0526; A61N 1/0529; A61N 1/36075; A61N 1/3606; A61N 1/36057; A61N 1/36146; A61N 1/0531; A61N 1/3603; A61N 1/36092; A61N 1/36128; A61N 1/36; A61N 1/00; A61N 1/04; A61N 1/18; A61N 1/37514; A61N 1/02; A61B 5/4836
See application file for complete search history.

(56) References Cited

U.S. PATENT DOCUMENTS

| | | | |
|---|---|---|---|
| 2006/0122454 A1 | 6/2006 | Riehl et al. | |
| 2007/0173908 A1 | 7/2007 | Begnaud | |
| 2014/0330336 A1* | 11/2014 | Errico | A61N 1/3756 607/45 |
| 2019/0046794 A1 | 2/2019 | Goodall et al. | |

* cited by examiner

*Primary Examiner* — Deborah L Malamud
(74) *Attorney, Agent, or Firm* — Cesari and McKenna, LLP

(57) ABSTRACT

A method of reducing cortical spreading depolarization in an animal having a brain injury includes: affixing to the animal one or more electrodes that are electrically connected to a neurostimulation device; and providing to the animal, by the neurostimulation device, via the one or more electrodes, electrical stimulation of the animal's trigeminal nerve, thereby reducing cortical spreading depolarization in the animal. The method may reduce at least one detrimental effect of cortical spreading depolarization on the injured animal brain.

18 Claims, 7 Drawing Sheets

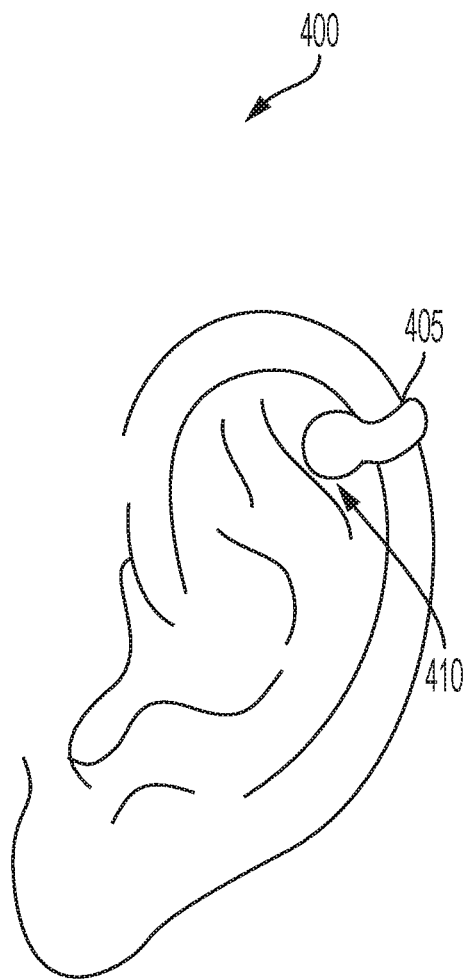
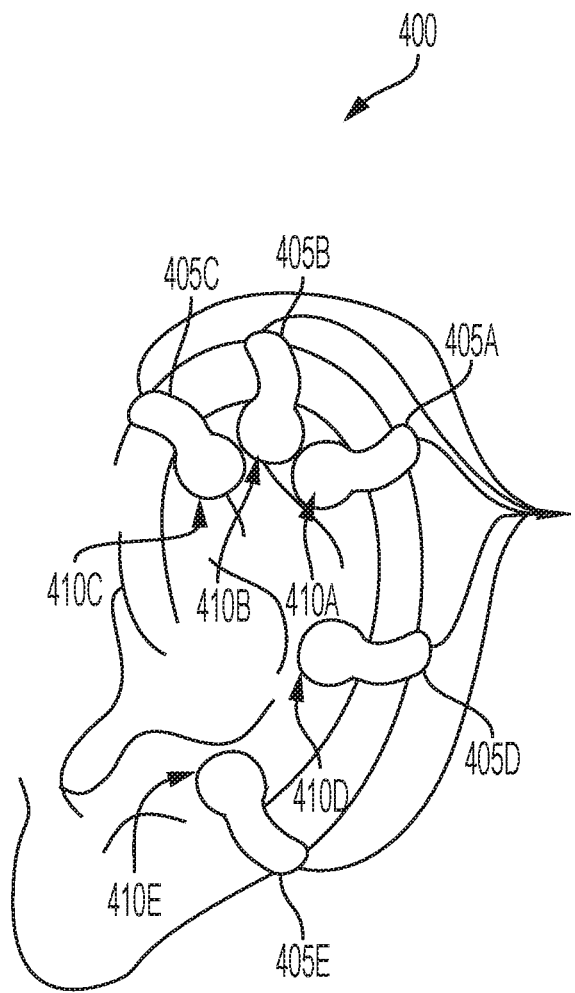
FIG. 4A
FIG. 4B

SYSTEMS AND METHODS FOR DELIVERING NEUROMODULATION TO REDUCE CORTICAL SPREADING DEPOLARIZATION IN ANIMALS INCLUDING HUMANS

STATEMENT REGARDING FEDERALLY SPONSORED RESEARCH OR DEVELOPMENT

This invention was made with government support under grant no. W81XWH-18-1-0773 awarded by the Department of Defense. The government has certain rights in the invention.

CROSS-REFERENCE TO RELATED APPLICATIONS

This application is a National Stage Application under 35 U.S.C. § 371 of International Application No. PCT/US19/29382, filed Apr. 26, 2019, the entire disclosure of which is incorporated herein by reference.

FIELD OF THE INVENTION

The invention relates generally to systems and methods for therapeutic neurostimulation of animals including humans. More specifically, the invention relates to systems and methods for non-invasive neurostimulation of an animal's trigeminal nerve in order to reduce the secondary effects of acute brain injuries.

BACKGROUND OF THE INVENTION

Cortical spreading depolarization (CSD) is a neurophysiological phenomenon of depressed electrical activity that spreads slowly through the brain from the site of injury and propagates dysfunction to vulnerable adjacent brain regions. CSD occurs spontaneously in the cerebral cortex of stroke, traumatic brain injury (TBI), and subarachnoid hemorrhage patients. Accumulating evidence shows that the expansion of ischemic territory is closely coupled to the occurrence of CSDs, due at least in part to the increased metabolic demand of repolarization. The occurrence of CSDs in association with acute brain injury has only been recognized in the past few years, and they are believed to cause further "secondary" brain damage. Currently, there is a paucity of pharmacological interventions to prevent CSDs, and the medications that do exist have significant side effects. Therefore, new strategies are needed to selectively reduce the deleterious consequences of CSDs in injured brains.

SUMMARY OF THE INVENTION

The invention, in various embodiments, features systems and methods for delivering electrical trigeminal nerve stimulation (TNS) to an animal (e.g., a human) in order to reduce the occurrence, duration and/or spread of CSDs so as to eliminate their adverse effects on the injured brain, as well as on the surrounding normal brain. Whether or not injury occurs after CSDs depends greatly on the capacity of tissues to re-establish ionic gradients (the repolarization phase) in the aftermath of CSDs. This capacity is influenced by the availability of adenosine triphosphate (ATP) and the ability of a brain region to increase cerebral blood flow (CBF) to match energy demands after CSDs. This increased demand can be variable, and in many instances can be quite large. While CSD is not always harmful, if the brain is unable to compensate for the increase in demand for energy substrates, then further damage is highly likely.

The trigeminal nerve is the largest cranial nerve, and the pathways from the trigeminal nerve project to a range of targets within the brainstem and beyond, forming an extensive network of connections throughout the central nervous system (CNS). The trigeminal nerve includes both afferent and efferent fibers. It is divided into three main branches—ophthalmic, maxillary and mandibular—that are connected to the sympathetic (SNS) and parasympathetic (PNS) autonomic nervous systems in the brain. The autonomic nervous system controls most of the body's functions over which animals do not have voluntary control, including heart rate, blood pressure and cerebral blood flow. This anatomy is believed to be the basis of the 'diving response'—an intriguing phenomenon seen in mammals such as dolphins and whales that allows them to spend prolonged periods of time under water—whose primary role is to conserve oxygen for sensitive brain and heart tissue. The trigeminal nerve is unique because of its intimate connection with cerebral and meningeal blood vessels, referred to as the trigemino-cerebrovascular system.

The inventors have previously shown that electrical stimulation of the trigeminal nerve not only increases cerebral blood flow (CBF) but also significantly increases brain oxygen tension ($P_{br}O_2$) in the brains of normal, TBI, and hemorrhagic shock rats. See, e.g., International Patent Application No. PCT/US2018/028622, filed on Apr. 20, 2018 and entitled "Systems and Methods for Delivering Non-Invasive Neuromodulation to Reduce the Effects of Shock and Traumatic Brain Injury in Animals and Humans and to Prolong Life," the contents of which are hereby incorporated by reference in their entirety. Additionally, TNS in normal brains was shown to increase the threshold current required for eliciting chemically-induced CSD by 129% and slow its propagation velocity by 28% ($p<0.01$ for each). Furthermore, TNS treatment immediately before middle cerebral artery occlusion (MCAO) in rats decreased infarction volumes by ~34% ($p<0.01$), increased CSD latency 7-fold, and decreased the numbers of CSDs by 53% ($p<0.001$).

The present invention provides novel methods to selectively reduce the deleterious consequences of CSDs with trigeminal nerve stimulation (TNS) employing the concept of ultra-precision medicine to protect the injured brain. In some embodiments, after brain injury, intermittent constant TNS can be delivered. In some embodiments, TNS can be delivered after, and/or only upon, CSD detection (e.g., every time a CSD has been detected by continuous monitoring). The cumulative experimental and clinical evidence suggest that CSD is both a real-time marker of injury and a mechanism for the development of secondary brain damage in several types of acute brain injury. As such, neuroprotective therapies that block CSD can reduce brain damage. TNS may block CSD in healthy and injured brains, and the deleterious consequences of CSDs in the injured brain may be selectively reduced while keeping their beneficial effects for the surrounding healthy tissues, e.g., by initiating cerebral vasodilation and increasing energy substrate levels for quicker repolarization.

In one aspect, the invention features a method of reducing cortical spreading depolarization in an animal (e.g., a human) having a brain injury. The method includes affixing to the animal one or more electrodes that are electrically connected to a neurostimulation device. The method also includes providing to the animal, by the neurostimulation device, via the one or more electrodes, electrical stimulation of the animal's trigeminal nerve, thereby reducing cortical spreading depolarization in the animal (e.g., in a "closed loop device").

In some embodiments, a detrimental effect of cortical spreading depolarization on the injured animal brain is reduced. In some embodiments, the electrical stimulation is provided during intermittent intervals after the animal has suffered the brain injury. In some embodiments, the electrical stimulation is provided for 5 to 60 minutes daily for a period of one week to six weeks. In some embodiments, the method includes (i) monitoring in real-time cortical spreading depolarization in the animal, by a biosensor that is in electronic communication with the neurostimulation device and (ii) providing, by the neurostimulation device, the electrical stimulation in response to detecting an indication of cortical spreading depolarization. In some embodiments, the detected indication of cortical spreading depolarization includes at least one of the following: decreased electrical activity in the brain, or decreased oxygen levels in the brain.

In some embodiments, reducing cortical spreading depolarization includes reducing at least one of the following for cortical spreading depolarization: incidence rate by at least 30%; or propagation speed by at least 15%. In some embodiments, reducing cortical spreading depolarization includes reducing at least one of a duration or an amplitude of each wave of CSD. In some embodiments, the reducing cortical spreading depolarization includes increasing a threshold current required for eliciting cortical spreading depolarization in the animal by at least 50%.

In some embodiments, the electrical stimulation is provided non-invasively. In some embodiments, the one or more electrodes are affixed to at least one of the following: the animal's tongue, forehead, cheeks, nose, outer ear (e.g., pinna), or other facial skin. In some embodiments, the cortical spreading depolarization is modulated in at least one of the following regions of the animal: the periaqueductal gray, the locus coeruleus, the raphe nuclei, the nucleus of the solitary tract, the rostral ventrolateral medulla, the cerebellum, the cortex, and the ventral posterior medial thalamus. In some embodiments, the electrical stimulation induces cerebral vasodilation in the animal. In some embodiments, the electrical stimulation activates a diving reflex (e.g., increased systemic blood pressure, cerebral vasodilation, increased cerebral blood flow, decreased heart rate, decreased respiratory rate, etc.) in the animal. In some embodiments, providing the electrical stimulation helps the animal conserve at least one of the following: oxygen or adenosine triphosphate in or near the animal's brain.

In some embodiments, the electrical stimulation provides a corrective to a distorted brain autoregulation mechanism of the animal, thereby reducing further brain damage. In some embodiments, the electrical stimulation has a frequency of 5-140 Hz. In some embodiments, the electrical stimulation has an intensity of 1-20 V. In some embodiments, the electrical stimulation has a duty cycle of 1 second "on" and 1-5 seconds "off". In some embodiments, the electrical stimulation includes a pulse width of 0.25-1 ms.

BRIEF DESCRIPTION OF THE DRAWINGS

The advantages of the invention described above, together with further advantages, may be better understood by referring to the following description taken in conjunction with the accompanying drawings. The drawings are not necessarily to scale; emphasis is instead generally placed upon illustrating the principles of the invention.

FIGS. 4A-4B show a human patient receiving non-invasive neurostimulation of the trigeminal nerve via targeting of the auricular branch of the trigeminal nerve using one pair of electrodes, according to an illustrative embodiment of the invention.

DETAILED DESCRIPTION

Figure 1A:
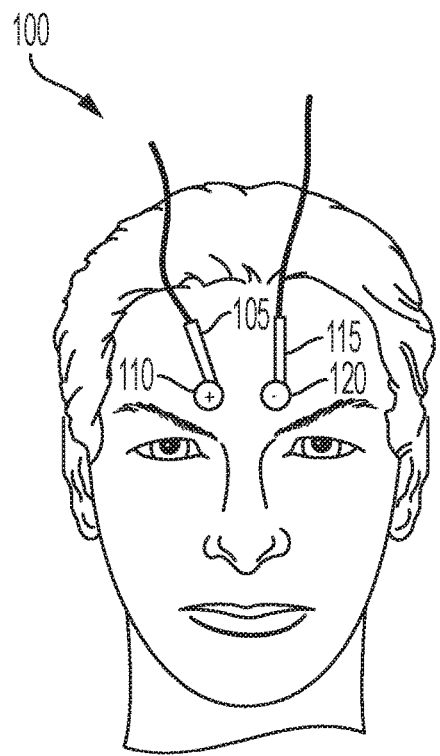
FIG. 1A shows a human patient receiving non-invasive neurostimulation of the trigeminal nerve via targeting of the ophthalmic division using one pair of electrodes, according to an illustrative embodiment of the invention.

FIG. 1A shows a human patient 100 receiving non-invasive neurostimulation of the trigeminal nerve via targeting of the ophthalmic division (the first major division of the trigeminal nerve that supplies the skin over the forehead and around the eyes) using one pair of electrodes, according to an illustrative embodiment of the invention. A first electrode 105 is placed on a first location 110 on the patient's face and a second electrode 115 is placed on a second location 120 on the patient's face. The ophthalmic division is reachable via the first location 110 and the second location 120.

Figure 3A:
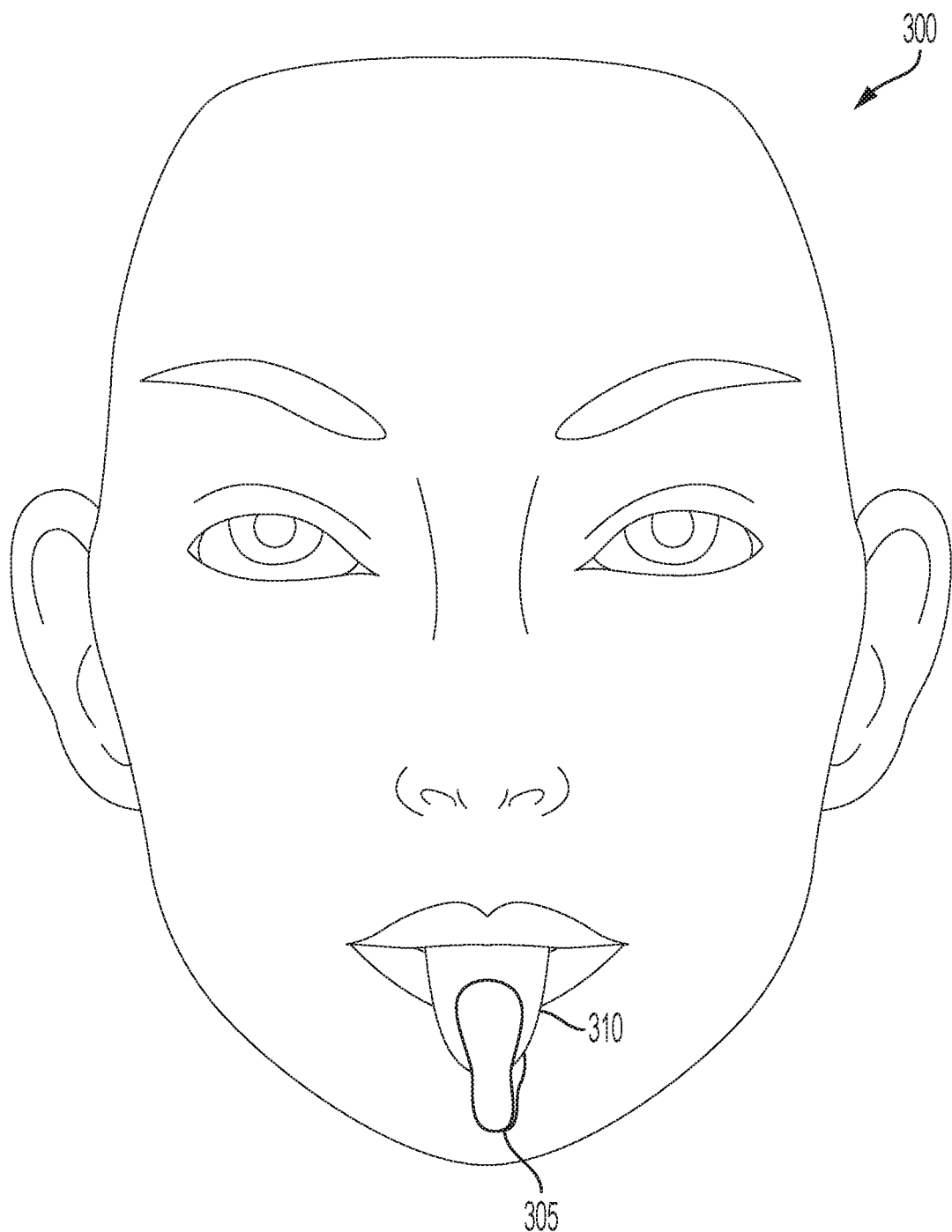
FIG. 3A shows a human patient receiving non-invasive neurostimulation of the trigeminal nerve via targeting of the mandibular division using one pair of electrode arrays, according to an illustrative embodiment of the invention.

Electrical stimulation of the trigeminal nerve is delivered in the supraorbital or infraorbital region of the face (e.g., using one pair of electrodes, cathode and anode, over the right and left side), using surface stimulation electrodes connected to a constant current/voltage stimulator (e.g., using a device shown and described in FIG. 3A herein). Rectangular-wave pulses (e.g., 0.05-1 ms duration) are delivered for variable durations (e.g., 0.5-2 min) at variable time intervals (e.g., 3-20 min), and stimulus intensity is set to decrease the heart rate by 10-30% as compared to a baseline heart rate (pre-stimulation). Electrical stimulation can be provided using, for example, an A-M Systems Model 2100 Isolated Pulse Stimulator (in this setup or others described herein).

Figure 1B:
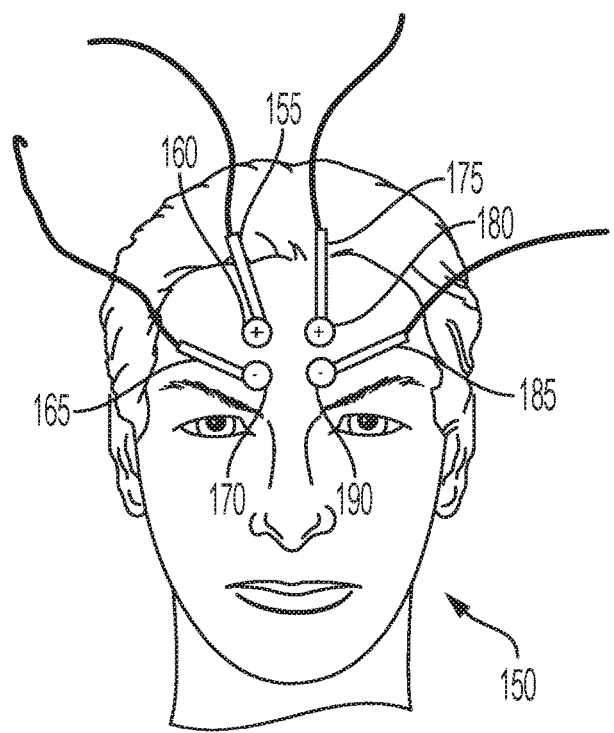
FIG. 1B shows a human patient receiving non-invasive neurostimulation of the trigeminal nerve via targeting of the ophthalmic division using two pairs of electrodes, according to an illustrative embodiment of the invention.

FIG. 1B shows a human patient 150 receiving non-invasive neurostimulation of the trigeminal nerve via targeting of the ophthalmic division using two pairs of electrodes, according to an illustrative embodiment of the invention. A first electrode 155 is placed on a first location 160 of the patient's face, and a second electrode 165 is placed on a second location 170 of the patient's face. A third electrode 175 is placed on a third location 180 of the patient's face, and a fourth electrode 185 is placed on a fourth location 190 of the patient's face. The maxillary division is reachable via the first location 160, the second location 170, the third location 180, and the fourth location 190, and is connected to the main trunk of the trigeminal nerve.

Electrical stimulation of the trigeminal nerve is delivered in the supraorbital or infraorbital region of the face (e.g., using two pair of electrodes, cathode and anode, over the right and left branch), using surface stimulation electrodes connected to a constant current/voltage stimulator (e.g., using a device shown and described in FIG. 3A herein). As above, rectangular-wave pulses (e.g., 0.05-1 ms duration) are delivered for variable durations (e.g., 0.5-2 min) at variable time intervals (e.g., 3-20 min), and stimulus intensity is set to decrease the heart rate by 10-30% as compared to a baseline heart rate (pre-stimulation). Electrical stimulation can be provided using, for example, an A-M Systems Model 2100 Isolated Pulse Stimulator (in this setup or others described herein).

Figure 2A:
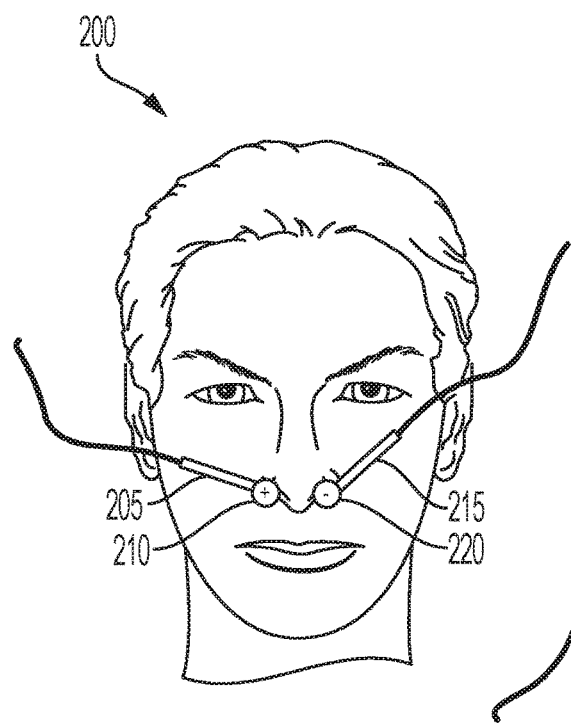
FIG. 2A shows a human patient receiving non-invasive neurostimulation of the trigeminal nerve via targeting of the maxillary division using one pair of electrodes, according to an illustrative embodiment of the invention.

FIG. 2A shows a human patient 200 receiving non-invasive neurostimulation of the trigeminal nerve via targeting of the maxillary division (the second major division of the trigeminal nerve that supplies the skin over the cheeks) using one pair of electrodes, according to an illustrative embodiment of the invention. A first electrode 205 is placed on a first location 210 on the animal's face and a second electrode 215 is placed on a second location 220 on the animal's face. The maxillary division is reachable via the first location 210 and the second location 220 and, like the ophthalmic division, is also connected to the main trunk of the trigeminal nerve.

Electrical stimulation of the trigeminal nerve is delivered via the branches of the ophthalmic division of the trigeminal nerve (e.g., using one pair of electrodes, cathode and anode, over the right and left branch), using surface stimulation electrodes connected to a constant current/voltage stimulator (e.g., using a device shown and described in FIG. 3A herein). Rectangular-wave pulses (0.05-1 ms duration) are delivered for variable durations (0.5-2 min) at variable time intervals (3-20 min), and stimulus intensity is set to decrease the heart rate by 10-30% as compared to a baseline heart rate (pre-stimulation).

Figure 2B:
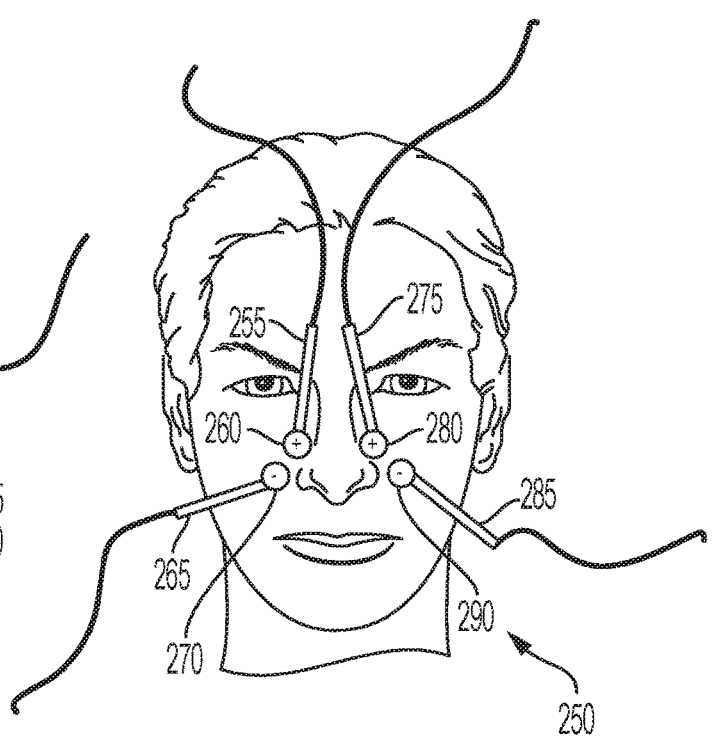
FIG. 2B shows a human patient receiving non-invasive neurostimulation of the trigeminal nerve via targeting of the maxillary division using two pairs of electrodes, according to an illustrative embodiment of the invention.

FIG. 2B shows a human patient 250 receiving non-invasive neurostimulation of the trigeminal nerve via targeting of the maxillary division using two pairs of electrodes, according to an illustrative embodiment of the invention. A first electrode 255 is placed on a first location 260 of the animal's face, and a second electrode 265 is placed on a second location 270 of the animal's face. A third electrode 275 is placed on a third location 280 of the animal's face, and a fourth electrode 285 is placed on a fourth location 290 of the animal's face. The maxillary nerve is reachable via the first location 260, the second location 270, the third location 280, and the fourth location 290, and is connected to the trigeminal nerve.

Electrical stimulation of the trigeminal nerve is delivered via branches of the ophthalmic division of the trigeminal nerve (e.g., using two pairs of electrodes, cathode and anode, over the right and left branch), using surface stimulation electrodes connected to a constant current/voltage stimulator (e.g., using a device shown and described in FIG. 3A herein). Rectangular-wave pulses (0.05-1 ms duration) are delivered for variable durations (0.5-2 min) at variable time intervals (3-20 min), and stimulus intensity is set to decrease the heart rate by 10-30% as compared to a baseline heart rate (pre-stimulation).

FIG. 3A shows a human patient 300 receiving non-invasive neurostimulation of the trigeminal nerve via targeting of the mandibular division (the third major division of the trigeminal nerve) using one or more electrodes, according to an illustrative embodiment of the invention. An electrode 305 is placed on the animal's tongue 310. The mandibular division is reachable via the animal's tongue 310 and, like the ophthalmic division, is also connected to the main trunk of the trigeminal nerve.

Figure 3B:
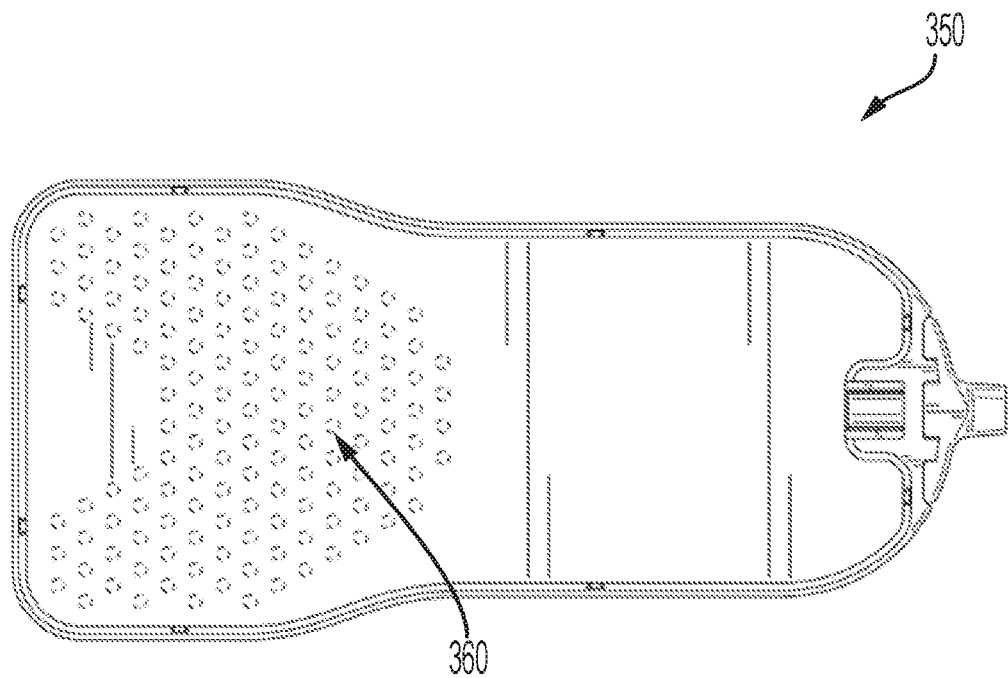
FIG. 3B shows a bottom view of a mouthpiece having electrodes for providing electrical stimulation to an animal, according to an illustrative embodiment of the invention.

FIG. 3B shows a bottom view of a mouthpiece 350 having electrodes 360 (e.g., in an array as shown) for providing electrical stimulation to an animal (e.g., to the tongue of a human), according to an illustrative embodiment of the invention. Electrical stimulation or current can be transmitted to the electrode array 360 by way of drive circuitry (not shown) connected to the mouthpiece 350 via a wire or a wireless connection. Current can be provided according to numerous methods, for example in a specific pattern of electrical pulses or in a random pattern. Different electrodes can be active at different times and can carry different currents at different times. Delivered current can stimulate the animal's trigeminal nerve. Examples of the design details of such mouthpieces can be found in U.S. Pat. No. 9,227,051, filed on Dec. 3, 2014 and entitled "Devices for Delivering Non-Invasive Neuromodulation to a Patient," and U.S. Pat. No. 9,072,889, filed on Dec. 3, 2014 and entitled "Systems and Methods for Providing Non-Invasive Neurorehabilitation of a Patient," the contents of which are hereby incorporated by reference in their entireties.

FIGS. 4A-4B show a human patient 400 receiving non-invasive neurostimulation of the trigeminal nerve via targeting of the auricular branch of the trigeminal nerve using one or more electrodes, according to an illustrative embodiment of the invention. An electrode 405 is placed on a first location 410 on the animal's ear. The auricular branch of the trigeminal nerve is reachable via the first location 410 and, like the ophthalmic division, is also connected to the main trunk of the trigeminal nerve. In some embodiments, multiple electrodes 405A-405E are attached to multiple locations 410A-410E on the animal's ear.

Figure 5:
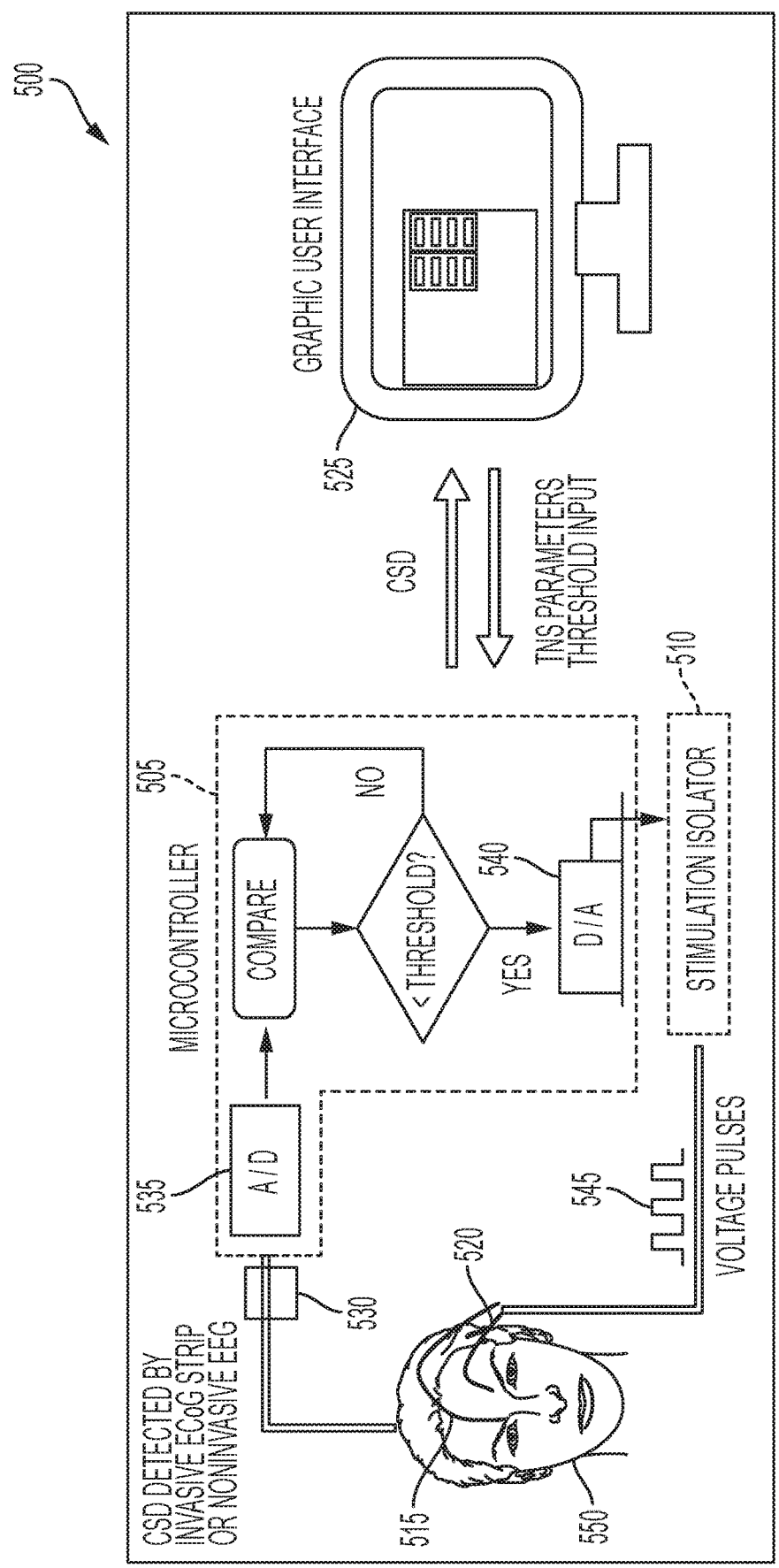
FIG. 5 shows a device for providing non-invasive neurostimulation of the trigeminal nerve using a closed-loop system that reacts to the patient's pathophysiologic brain activity of CSD, according to an illustrative embodiment of the invention.

FIG. 5 shows a device 500 for providing non-invasive neurostimulation of the trigeminal nerve (e.g., according to the methods shown and described above) using a closed-loop system that reacts to the patient's pathophysiologic brain activity of CSD (e.g., as recorded in an ECoG/EEG waveform), according to an illustrative embodiment of the invention. The device 500 can be an automated closed-loop resuscitation system including a microcontroller 505, a stimulation isolator 510 in electrical communication with the microcontroller 505, electrodes 515, 520 in electrical communication with the stimulation isolator 510, a graphic user interface (GUI) 525 in electrical communication with the microcontroller 505, and an ECoG/EEG signal recording system 530 in electrical communication with the microcontroller 505. The microcontroller can include an analog to digital converter (A/D) 535 and a digital to analog (D/A) converter 540. The microcontroller 505 can have circuitry and/or software programming for causing non-invasive trigeminal nerve stimulation to be triggered in the stimulation isolator 510 using a physiologic feedback loop, based on, for example: blood pressure; heart rate; respiration rate; pulse rate; arterial oxygen saturation; plethysmography; central venous pressure; transcranial doppler; and/or near infrared spectroscopy (e.g., cranial diffusions). In some embodiments, the device can include skin-applied adhesive electrodes.

During operation, the ECoG/EEG signal recording system 530 and its analog front-end record arterial pressure of an animal (e.g., a human patient) 550 and send it to the microcontroller 505. The analog to digital converter (A/D) 535 of the microcontroller 505 samples the recorded pressure signal and compares it with a threshold value preset by a user via the GUI 525. When the recorded signal is lower than the threshold, the digital to analog (D/A) converter 540 of the microcontroller 505 sends voltage and/or current pulses with given parameters preset by the GUI 525 to the current stimulation isolator 510 (e.g., amplitude). The stimulation isolator 510 delivers the stimulation voltages 545 to the trigeminal nerve (e.g., via the face) using a stimulation electrode (e.g., 515 or 520). The stimulation of the trigeminal nerve decreases the heart rate until the sampled heart rate signal is equal to the targeted value (10-30% decrease of pre-stim heart rate). Meanwhile, the microcontroller 505 also transmits the recorded heart rate signal to the GUI 525 through a universal asynchronous receiver transmitter (UART) known in the art (not shown) for real-time monitoring and reference.

Figure 6:
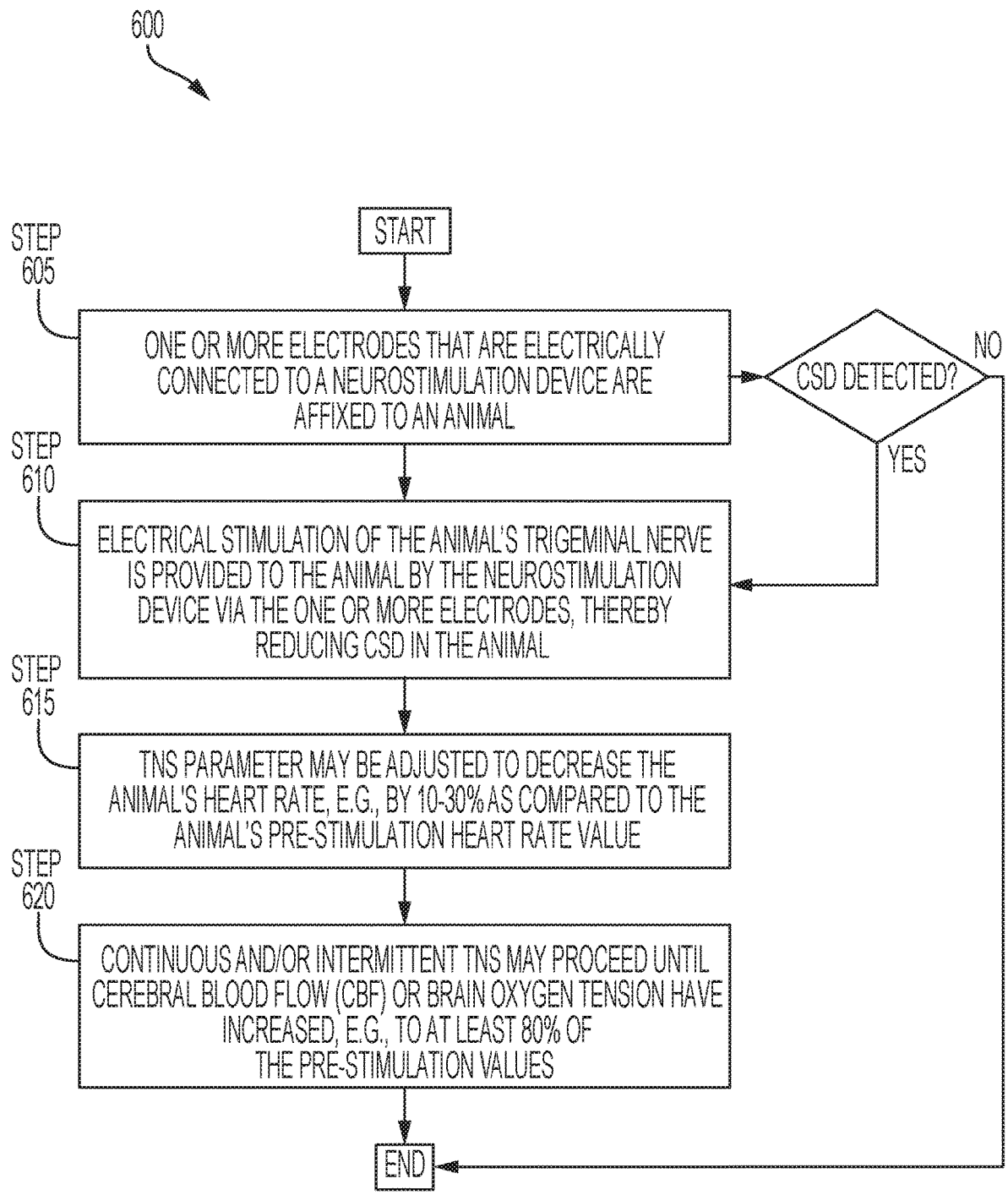
FIG. 6 shows a flow chart of a method for providing non-invasive neurostimulation of an animal's trigeminal nerve in response to detecting a CSD waveform, thereby reducing cortical spreading depolarization in an animal, according to an illustrative embodiment of the invention.

FIG. 6 shows a flow chart 600 of a method for providing non-invasive neurostimulation of an animal's trigeminal nerve in response to detecting a CSD waveform, thereby reducing cortical spreading depolarization in an animal, e.g., a human, according to an illustrative embodiment of the invention. In a first step 605, one or more electrodes (e.g., ECoG or EEG electrodes) that are electrically connected to a neurostimulation device are affixed to the animal (e.g., to detect CSDs). In a second step 610, electrical stimulation of the animal's trigeminal nerve is provided to the animal by the neurostimulation device, via the one or more electrodes (e.g., via contact with the animal's skin), thereby reducing cortical spreading depolarization in the animal. In a third step 615 (optional), one or more TNS parameters may be adjusted to decrease the animal's heart rate, e.g., by 10-30% as compared to the animal's pre-stimulation heart rate. In a fourth step 620 (optional), continuous and/or intermittent TNS may proceed until cerebral blood flow (CBF) or brain oxygen tension have increased, e.g., to at least 80% of the pre-stimulation values.

In some embodiments, CSDs are detected by invasive or non-invasive electrodes, and a signal is transmitted to an analog to digital (A/D) converter. In some embodiments, if CSDs are detected, a stimulus is generated and conveyed to a trigeminal nerve area (e.g., of the face, external ear, or tongue). In some embodiments, a drop in the animal's heart rate indicates that a diving reflex has been generated and will cause the system to suppress the stimulation. In some embodiments, CSDs can be detected by one or more invasive ECoG strips that are laid on the brain surface, or by noninvasive EEG.

Experimental results showing the effectiveness of the above systems and methods have been obtained in male Sprague-Dawley rats. Studies were performed on seven such rats weighing between 250 and 325 grams each. The rats were randomized into two study groups: (1) sham-operated control rats; and (2) rats receiving 15 minute deliveries of TNS at intermittent intervals. Electrical stimulation of the rats' trigeminal nerves was performed by introducing two needles (26 GA) subcutaneously, bilaterally along an imaginary line connecting the ear and eye of the rats. Rectangular cathodal pulses of 0.5 ms each were delivered by an electrical stimulator operating at 25 Hz and 5V continuously for 15 minutes. Sham controls had identical electrode placements but did not provide any electrical stimulation. Susceptibility to CSD was evaluated by measuring the electrical threshold for CSD, followed by analysis of CSD frequency and propagation speed during continuous topical application of 1M KCl solution for one hour.

The experimental results showed that TNS increased the threshold current for eliciting CSD by 114% (0.7±0.3 μC vs. 1.5±0.6 μC; n=3 p<0.05; sham vs. TNS), slowed its propagation velocity by 28% (7.4±0.8 mm/min vs. 5.3±0.6 mm/min; n=4, p<0.05; sham vs. TNS), and reduced the frequency of CSD during continuous topical 1M KCl by 42% (12.7±2.1 CSDs/h vs. 7.3±1.5 CSDs/h; n=4, p<0.05; sham vs. TNS). The results demonstrate that electrical TNS effectively suppresses CSD susceptibility and therefore can serve as a new class of neuroprotective treatments for a variety of brain injuries.

In the middle cerebral artery occlusion (MCAO) stroke model, TNS pre-treatment didn't alter the amplitude or duration of each CSD. However, TNS significantly lengthened the latency until the appearance of the first CSD almost 7-fold, and decreased their number by 53% (3.8±0.8 vs. 8.2±2.1; n=6). 1 h TNS pretreatment just before MCAO also significantly reduced infarction volumes by 34% (from 218.5±42.6 to 143.1±24.7 mm3; n=6).

A controlled cortical impact (CCI) model was used to create severe TBI in male Sprague-Dawley rats. Animals were randomized to four study groups: (1) sham; (2) TBI control; (3) TBI rats with intermittent TNS (open-loop); and (4) TBI rats with targeted TNS (closed-loop). TNS was performed by introducing two Teflon-coated bipolar wires bilaterally for 3 hours. The number of CSDs were recorded. Brain tissues were collected at 24 h after TBI to measure the edema and lesion volumes. Both open-loop and closed-loop TNS following TBI significantly decreased the CSD numbers by 60% and 49% in the injured brain (7.2±0.8 vs. 2.9±0.6 vs. 3.7±1.1 CSDs; n=6-7; p<0.05; control vs. open-loop TNS vs. closed-loop TNS), respectively. Furthermore, in the TNS-treatment group, there was a significant decrease in brain edema (82.4±0.8% vs. 80.2±0.6% vs. 79.6±1.2%; n=7-8, p<0.05) and lesion volumes (12.5±1.8 mm3 vs. 7.7±1.4 vs. 8.4±2.3; n=7-8, p<0.05).

The innovative methods described herein enjoy the following advantages over previous neuroprotection approaches. First, using trigeminal nerve stimulation to reduce or prevent CSDs has not been described before. Second, the proposed approach will enable the targeting of individual CSD pathomechanisms in real-time, thereby delivering the specific desired therapeutic effects in real time. Third, selective targeting of individual CSDs will raise the chance of that the proposed approach can be combined with other neuroprotective approaches while minimizing complications and side effects. Thus, the proposed approach differs dramatically from prior neuroprotection approaches and offers the first opportunity to apply mechanistic targeting and personalized treatment principles to TBI, stroke, subarachnoid, and/or hemorrhage neuroprotection with the fewest possible side effects. Fourth, the development of a closed-loop system for the automated detection of CSD and delivery of TNS treatment will allow for the widespread adoption of the proposed approach to other diseases where CSD plays a significant role, including ischemic and hemorrhagic stroke, since CSD is a proven mechanism of lesion development and delayed neurologic deterioration, with an up to 80%-100% incidence in various stroke subtypes.

While the present technological concepts have been particularly shown and described above with reference to exemplary embodiments thereof, it will be understood by those of ordinary skill in the art, that various changes in form and detail can be made without departing from the spirit and scope of the present invention.

What is claimed is:

1. A method of reducing cortical spreading depolarization in an animal having a brain injury, the method comprising:
affixing to the animal one or more electrodes that are electrically connected to a neurostimulation device; and
providing to the animal, by the neurostimulation device, via the one or more electrodes, electrical stimulation of the animal's trigeminal nerve, thereby reducing cortical spreading depolarization in the animal; and
wherein the electrical stimulation induces cerebral vasodilation in the animal, activates a diving reflex in the animal, or both.

2. The method of claim 1 wherein a detrimental effect of cortical spreading depolarization on the injured animal brain is reduced.

3. The method of claim 1 wherein the electrical stimulation is provided during intermittent intervals after the animal has suffered the brain injury.

4. The method of claim 1 wherein the electrical stimulation is provided for 5 to 60 minutes daily for a period of one week to six weeks.

5. The method of claim 1 further including (i) monitoring, in real-time, cortical spreading depolarization in the animal, by a biosensor that is in electronic communication with the neurostimulation device, and (ii) providing, by the neurostimulation device, the electrical stimulation in response to detecting an indication of cortical spreading depolarization.

6. The method of claim 5 wherein the detected indication of cortical spreading depolarization includes at least one of the following: decreased electrical activity in the brain, or decreased oxygen levels in the brain.

7. The method of claim 1 wherein reducing cortical spreading depolarization includes reducing at least one of the following for cortical spreading depolarization: incidence rate by at least 30% or propagation speed by at least 15%.

8. The method of claim 1 wherein the reducing cortical spreading depolarization includes reducing at least one of a duration or an amplitude of each wave of cortical spreading depolarization.

9. The method of claim 1 wherein the reducing cortical spreading depolarization includes increasing a threshold current required for eliciting cortical spreading depolarization in the animal by at least 50%.

10. The method of claim 1 wherein the electrical stimulation is provided non-invasively.

11. The method of claim 1 wherein the one or more electrodes are affixed to at least one of the following: the animal's tongue, forehead, cheeks, nose, outer ear, or other facial skin.

12. The method of claim 1 wherein cortical spreading depolarization is modulated in at least one of the following regions of the animal: the periaqueductal gray, the locus coeruleus, the raphe nuclei, the nucleus of the solitary tract, the rostral ventrolateral medulla, the cerebellum, the cortex, and the ventral posterior medial thalamus.

13. The method of claim 1 wherein the electrical stimulation has a frequency of 5-140 Hz.

14. The method of claim 1 wherein the electrical stimulation has an intensity of 1-20 V.

15. The method of claim 1 wherein the electrical stimulation has a duty cycle of 1 second "on" and 1-2 seconds "off".

16. The method of claim 1 wherein the electrical stimulation includes a pulse width of 0.25-1 ms.

17. A method of reducing cortical spreading depolarization in an animal having a brain injury, the method comprising:
affixing to the animal one or more electrodes that are electrically connected to a neurostimulation device; and
providing to the animal, by the neurostimulation device, via the one or more electrodes, electrical stimulation of the animal's trigeminal nerve, thereby reducing cortical spreading depolarization in the animal and helping the animal conserve at least one of the following: oxygen or adenosine triphosphate in or near the animal's brain.

18. A method of reducing cortical spreading depolarization in an animal having a brain injury, the method comprising:
affixing to the animal one or more electrodes that are electrically connected to a neurostimulation device; and
providing to the animal, by the neurostimulation device, via the one or more electrodes, electrical stimulation of the animal's trigeminal nerve, thereby reducing cortical spreading depolarization in the animal; and
wherein the electrical stimulation provides a corrective to a distorted brain autoregulation mechanism of the animal, thereby reducing further brain damage.

* * * * *